(12) United States Patent
McIntyre et al.

(10) Patent No.: US 8,136,522 B2
(45) Date of Patent: Mar. 20, 2012

(54) CONTINUOUS POSITIVE AIRWAY PRESSURE DEVICE

(75) Inventors: Donald Ross McIntyre, Hillsborough, NC (US); Cindy McIntyre, legal representative, Hillsborough, NC (US); James Edward Miles, Graham, NC (US); Geoffrey Mark Shaw, Christchurch (NZ); Michael William Ryan, Dunedin (NZ); William Jesse Chaloner, Dunedin (NZ); Terence James Smith, Dunedin (NZ); Lawrence Gordon Alloo, Dunedin (NZ); Robert Charles Berry, Dunedin (NZ)

(73) Assignee: Lifevent Medical Limited (NZ)

( * ) Notice: Subject to any disclaimer, the term of this patent is extended or adjusted under 35 U.S.C. 154(b) by 747 days.

(21) Appl. No.: 11/993,992

(22) PCT Filed: Jul. 4, 2006

(86) PCT No.: PCT/NZ2006/000172
§ 371 (c)(1),
(2), (4) Date: Dec. 20, 2008

(87) PCT Pub. No.: WO2007/004903
PCT Pub. Date: Jan. 11, 2007

(65) Prior Publication Data
US 2009/0199852 A1 Aug. 13, 2009

(30) Foreign Application Priority Data

Jul. 4, 2005 (NZ) .................................. 541134
May 19, 2006 (NZ) .................................. 547346

(51) Int. Cl.
*A61M 16/00* (2006.01)
(52) U.S. Cl. ......... 128/205.13; 128/205.14; 128/205.15; 128/205.16; 128/205.17
(58) Field of Classification Search ............ 128/205.13–205.18, 201.18, 204.28
See application file for complete search history.

(56) References Cited

U.S. PATENT DOCUMENTS

| | | |
|---|---|---|
| 3,046,979 A | 7/1962 | Andreasen |
| 4,159,722 A | 7/1979 | Walker |
| 4,340,044 A | 7/1982 | Levy |
| 4,807,616 A * | 2/1989 | Adahan ................. 128/204.21 |
| 5,076,267 A | 12/1991 | Pasternack |
| 5,711,296 A | 1/1998 | Kolobow |
| 7,350,519 B2 * | 4/2008 | Duncan ................. 128/200.14 |

FOREIGN PATENT DOCUMENTS

| | | |
|---|---|---|
| EP | 0112979 | 7/1984 |
| WO | WO 02089886 | 11/2002 |

* cited by examiner

*Primary Examiner* — Glenn Richman
(74) *Attorney, Agent, or Firm* — Galbreath Law Offices, P.C.; John A. Galbreath

(57) ABSTRACT

A continuous positive airway pressure device which includes:—an inflatable breathable air reservoir provided with an air inlet/outlet;—a pressurized gas reservoir arranged to apply a predetermined substantially constant pressure on the breathable air reservoir, irrespective of the degree of inflation of the breathable air reservoir.

28 Claims, 15 Drawing Sheets

CONTINUOUS POSITIVE AIRWAY PRESSURE DEVICE

TECHNICAL FIELD

The present invention relates to a continuous positive airway pressure (CPAP) device, i.e. a device for supplying air or (more usually) an air/oxygen mixture at a positive, (i.e. above atmospheric) pressure, to a patient, and to an air reservoir apparatus for such a device. A CPAP machine may assist the lung function of a sick or injured patient by supplying air, generally oxygen enriched, at an above-atmospheric pressure, and/or may be modified to actively assist carbon dioxide removal from the lungs by using two levels of positive pressure. In the latter mode, the device functions as a ventilator and is capable of providing up to 100% of a patient's minute ventilation.

BACKGROUND ART

A number of continuous positive airway pressure devices are already known. Devices of this type currently being used in hospitals in first world countries generally require the supply of oxygen at high flow rates; since most modern hospitals have oxygen on tap and oxygen is available cheaply, a relatively wasteful use of oxygen is acceptable. However, in less developed countries or in out-of-hospital situations, (e.g. in ambulances, on battlefields, in emergency treatment stations) oxygen is available only in cylinders and a high rate of use of oxygen is unacceptable:—the cylinders simply are emptied too quickly.

It is therefore an object of the present invention to provide a continuous positive airway pressure device capable of operating at low flow rates of oxygen, whilst nevertheless reliably supplying the required air/oxygen mix to a patient.

In order to reduce the rate of the use of oxygen, it is necessary to use a reservoir built into the device. This is because the peak gas flow requirements of patient in acute respiratory distress can be anything from 60-120 liters per minute but practical engineering considerations mean that the gas flow rate through a portable continuous positive airway pressure device should be kept below 30 liters per minute. To make up the difference between gas demand and gas supply, portable devices must employ a storage system to store the gas while the patient is in between breaths or is breathing out. Any such storage system must be capable of a substantially constant pressure response, i.e. the pressure of the gas supply to the patient must not vary substantially whether the reservoir is full, part full or nearly empty.

A number of existing devices have the drawback that the pressure of the gas supply to the patient varies considerably depending upon whether the reservoir is nearly full, partly full or nearly empty. To overcome this drawback, a very much larger reservoir has to be used than is optimal for a portable device.

Some designs have been proposed to overcome this problem by providing a constant pressure response reservoir; see for example German Patent Nos. DE 3712389 and EP 0744184.

German patent No DE 371-2389 discloses a reservoir of flexible material the upper surface of which is weighted either by a weight or by a weighted lever. However, the reservoir does not incorporate any type of stabilizing device to ensure that, as the bellows is compressed and expanded, the weighting on the reservoir is kept even.

EP 0744184 discloses a reservoir at least partly of elastic material, preformed so that the reservoir itself supplies compression to its contents. Since the pressure applied by a reservoir of this design would fluctuate markedly depending upon the volume of gas contained in the reservoir (i.e. according to the degree of expansion of the reservoir) a reservoir of this design could not provide a gas at a uniform or substantially uniform pressure.

A further drawback to both of the above described designs is that they relate to relatively large and complex devices which would be unsuitable for use outside a hospital environment.

Russian patent 459243 and German patent DE 410-7666 both disclose a reservoir in the form of simple bellows which is weighted by an upper moving plate. The moving plate can slide towards or away from a baseplate along fixed vertical guides. The guides are rigid and extend the full height of the expanded reservoir, resulting in a bulky apparatus which cannot be regarded as portable except in a hospital environment.

Indeed, a marked drawback of all known designs is the bulk of the equipment. Some of the devices, of course, are not designed to be portable at all, but even those devices which technically are portable are relatively large, fragile and easily damaged. A device which is classed as "portable" for a hospital environment may nevertheless be completely unsuited to being thrown into the back of a truck or into an aircraft, and may be too bulky to be stored conveniently for emergency use.

The present applicant's earlier patent application NZ 511096/514278/515104 goes part way to overcoming the above described drawbacks but proved rather too heavy and bulky for fully portable use, and also was rather time-consuming to adjust for different air flows.

DISCLOSURE OF INVENTION

It is therefore a further object of the present invention to provide a continuous positive airway pressure device (CPAP) which can be stowed into a relatively small space, which is robust, lightweight and easily portable when not in use, and which can be easily adjusted for different required air flows.

Another object of the present invention is the provision of a CPAP device which in operation is minimally affected by gravity, so that the device can be operated effectively in wide range of orientations.

STATEMENT OF INVENTION

The present invention provides a continuous positive airway pressure device which includes:
  an inflatable breathable air reservoir provided with an air inlet/outlet;
  a pressurised gas reservoir arranged to apply a predetermined substantially constant pressure on the breathable air reservoir, irrespective of the degree of inflation of the breathable air reservoir.

Preferably, the pressurised gas reservoir applies said predetermined pressure on the breathable air reservoir by means of:
  a pneumatic ram which is operable by the pressurised gas reservoir; and
  load transmitting means connected to the pneumatic ram.

In a preferred form of the invention, the pneumatic ram incorporates a rolling diaphragm and the load transmitting means includes a movable plate arranged to apply pressure on the breathable air reservoir and cables and pulleys; one or more cables are connected between the movable plate and the pneumatic ram such that the reciprocation of the pneumatic ram causes corresponding movements of the plate.

The moveable plate may contact the upper or lower surface of the breathable air reservoir, and may be a rigid solid plate, a flexible solid plate, a rigid mesh plate or a flexible mesh plate.

The pressurised gas reservoir may include of a pressurised gas capsule or a separate high pressure reservoir or a separate high pressure reservoir connected to a pressurised gas capsule. Preferably, the pressurised gas reservoir also includes at least one low pressure reservoir. In one embodiment of the invention, the pressurised gas reservoir consists only of one or more low pressure reservoirs; in another embodiment of the invention, a pressurised gas reservoir includes both a high pressure and one or more low pressure reservoirs.

As used herein, the term "air" includes air, oxygen, air/oxygen mixtures and mixtures of air and/or oxygen with other gases and with therapeutic drugs or gene therapy or other preparations.

Preferably, the breathable-air reservoir is made of a flexible non-elastic material.

Gas supply to the device of the present invention can be delivered by any suitable gas delivery system, which includes, but is not limited to:—compressed air and/or oxygen from a piped system or from a cylinder; fan forced air and/or oxygen, supplied by any of a range of known equipment; compressed air/oxygen from a portable reservoir. It should be noted that a portable reservoir can be devised from any large capacity inflatable object, even one which is hand pumped, e.g. an inflatable mattress.

The device may be used with standard bore hose (internal diameter approximately 22 mm). However, it is preferred to use the device of the present invention with a wide bore hose (i.e. a hose of diameter between 30-55 mm internal diameter), since the combination of the device and wide bore hose provides apparatus in which the imposed work of breathing on a patient is largely independent of the fresh gas flow rate.

A further advantage of the present invention is that the above described device, used in combination with wide bore hose, may be used to deliver drug therapy and gene therapy, and hyperbaric treatments, and to provide portable CPAP to treat altitude sickness and acute pulmonary oedema (e.g. heart failure and lung injury). This particular advantage is made possible by the fact that the CPAP device of the present invention can operate at very low flow rates without loss of performance. Medication cannot normally be provided in combination with high flow CPAP devices because too much of the airflow is surplus to the patient's requirements in the patient simply does not breathe enough of the applied medication. The CPAP of the present invention is capable of operating at ranges of five liters per minute to 15 liters per minute or higher if required.

The device also is useful in intra-/post-operative applications where the patient has an increased oxygen requirement, (typically due to small areas of lung collapse). Further, the device is useful in the treatment of all cases of chronic airflow limitation or chronic airways disease, (or asthma).

For emergency/battlefield use, the device may be fitted with chemical absorbent or bacterial/viral/other biologically active particle filters, to protect the patient from toxic gases and/or biological weapons.

BRIEF DESCRIPTION OF THE DRAWINGS

By way of example only, preferred embodiments of the present invention are described in detail with reference to the accompanying drawings, in which:

FIG. 1 is an isometric view of a first embodiment of the present invention;

FIG. 2 is a diagram of the system for applying pressure to the bellows;

FIG. 3 is a side view of the bellows in the partially expanded condition;

FIG. 4 is a side view of the bellows alone;

FIG. 5 is a side view of part of FIG. 1, on a larger scale;

FIG. 6 is a diagram showing the system of pressure transmission from the pneumatic ram to the plate;

FIG. 7 is an isometric view of a second embodiment of the device of the present invention;

FIG. 8 is a plan view of the underside of the base of the device of FIG. 7;

FIG. 9 is a diagram showing the system of pressure transmission from the pneumatic ram to the pressure plate;

FIG. 10 is a side view of the bellows;

FIG. 11 is a view similar to FIG. 7, but with the bellows in place;

Referring to FIG. 1-6 of the drawings, a CPAP device 2 in accordance with a first embodiment of the present invention consists of a housing 3 which contains the pressurising system of FIG. 2 and a breathable-air reservoir in the form of a bellows 11 (see FIGS. 3 and 4), which are described in greater detail hereinafter. In FIG. 1, only the framework of the housing 3 is shown:—a top plate 4, a baseplate 5 in the form of a shallow tray with sides 5a, corner posts 6, and side supports 7. The top plate 4 and baseplate 5 both are rectangular and are the same size in plan. In the completed housing, the sides of the housing, i.e. the gaps between the corner posts 6, are filled in by protective side plates which are releasably secured to the corner posts 6.

Figure 1:
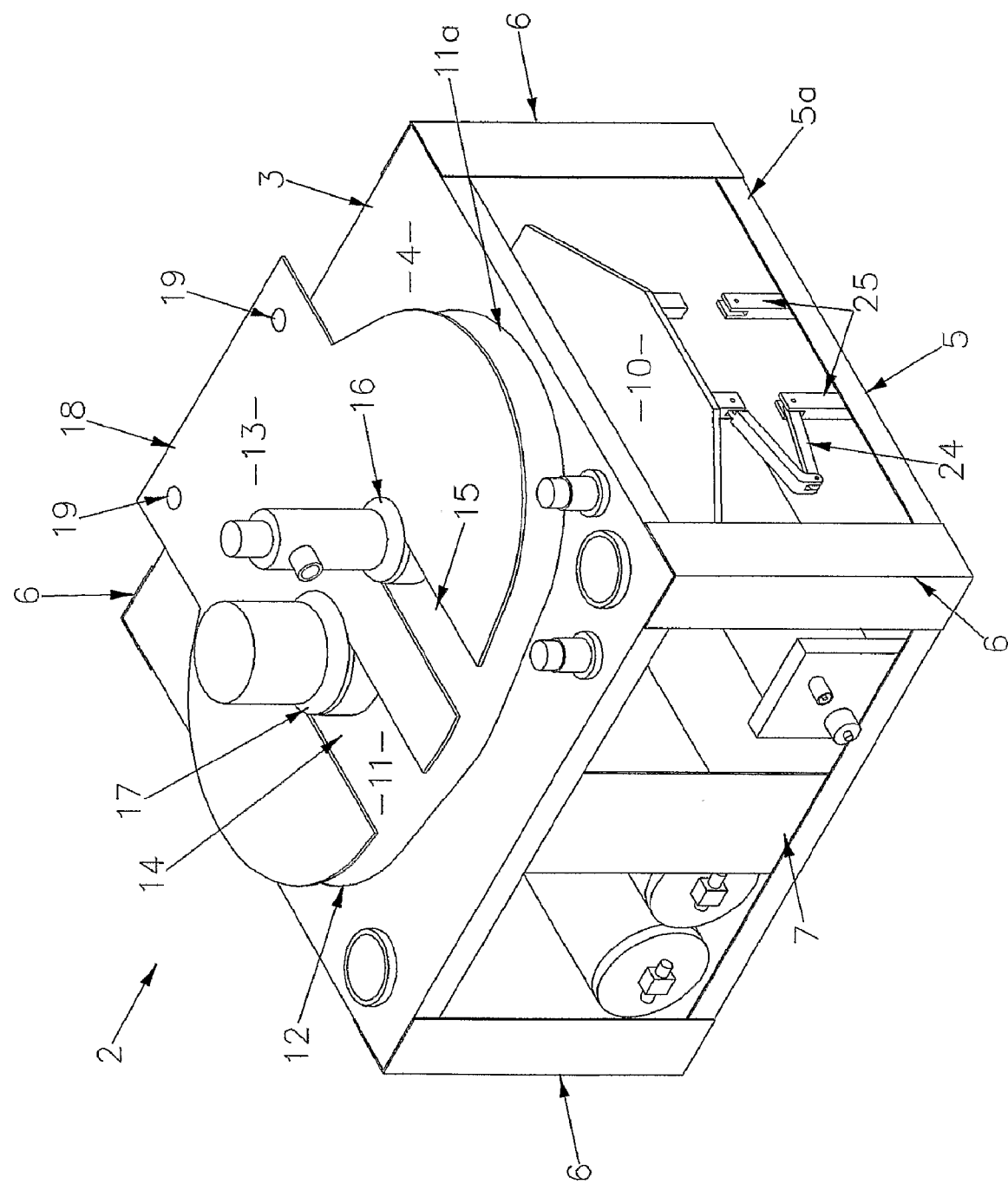
FIG. 1-6 relate to a first embodiment of the present invention.
Figure 2:
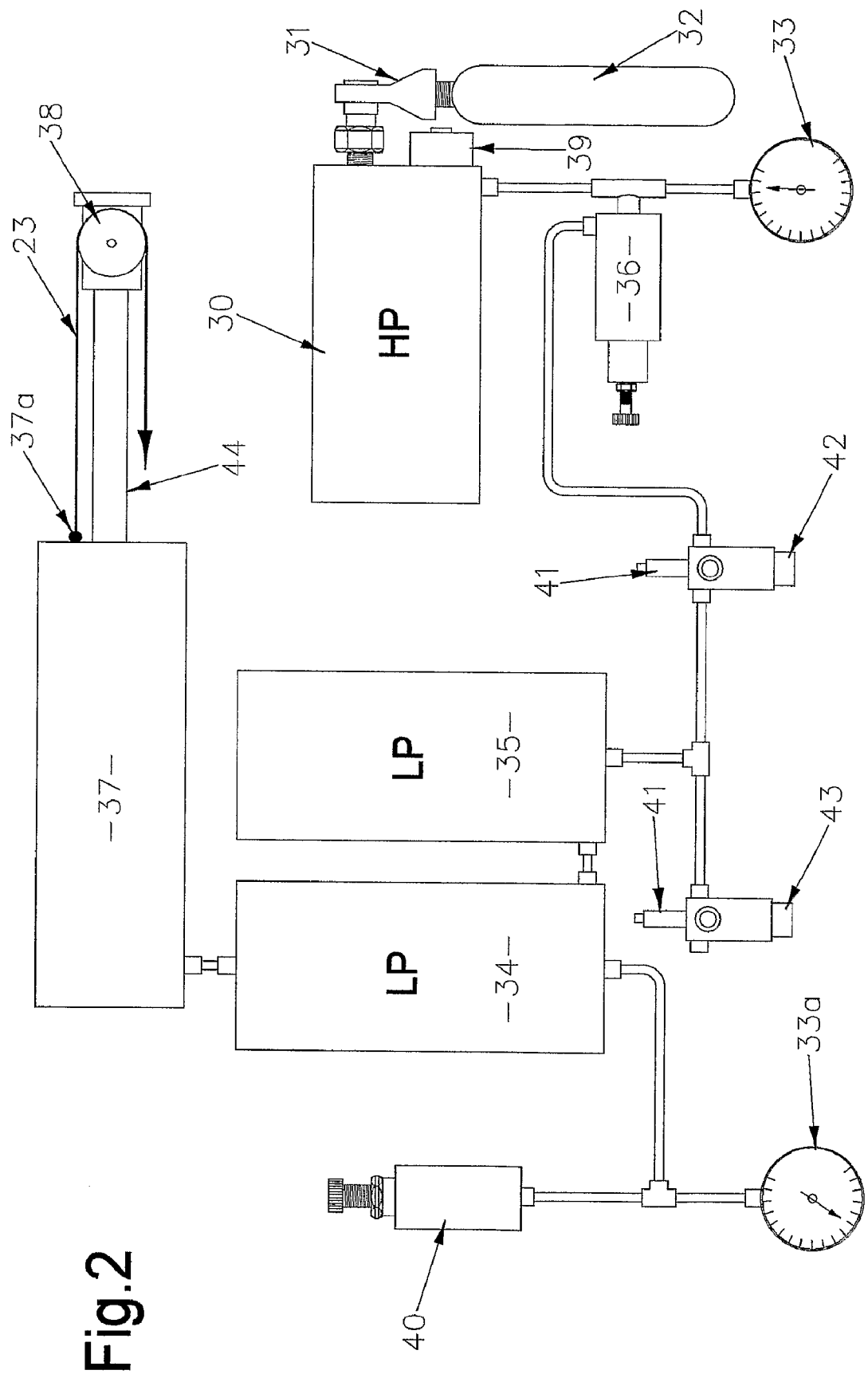

The pressurising system of FIG. 2 is mounted on the baseplate 5, with the lower support plate 10 carrying of the bellows 11 lying above the pressurising system, in a plane substantially parallel to the planes of the plate 4 and baseplate 5. The bellows 11 is shown in FIG. 1 its partly expanded condition with the upper surface 11a of the bellows extending a short distance through an aperture 12 cut in the top plate 4. A lid 13 rests on top of the upper surface of the bellows 11. The lid 13 is a flat rigid plate formed with two parallel open ended slots 14, 15; the lid 13 is held in position partly by the engagement of the sides of these slots with the sides of air inlet 16 and the air outlet 17, formed on the upper surface of the bellows 11. The lid 13 is dimensioned to completely cover the aperture 12 when the bellows is collapsed, and in this position acts as a cover for the device.

Figure 3:
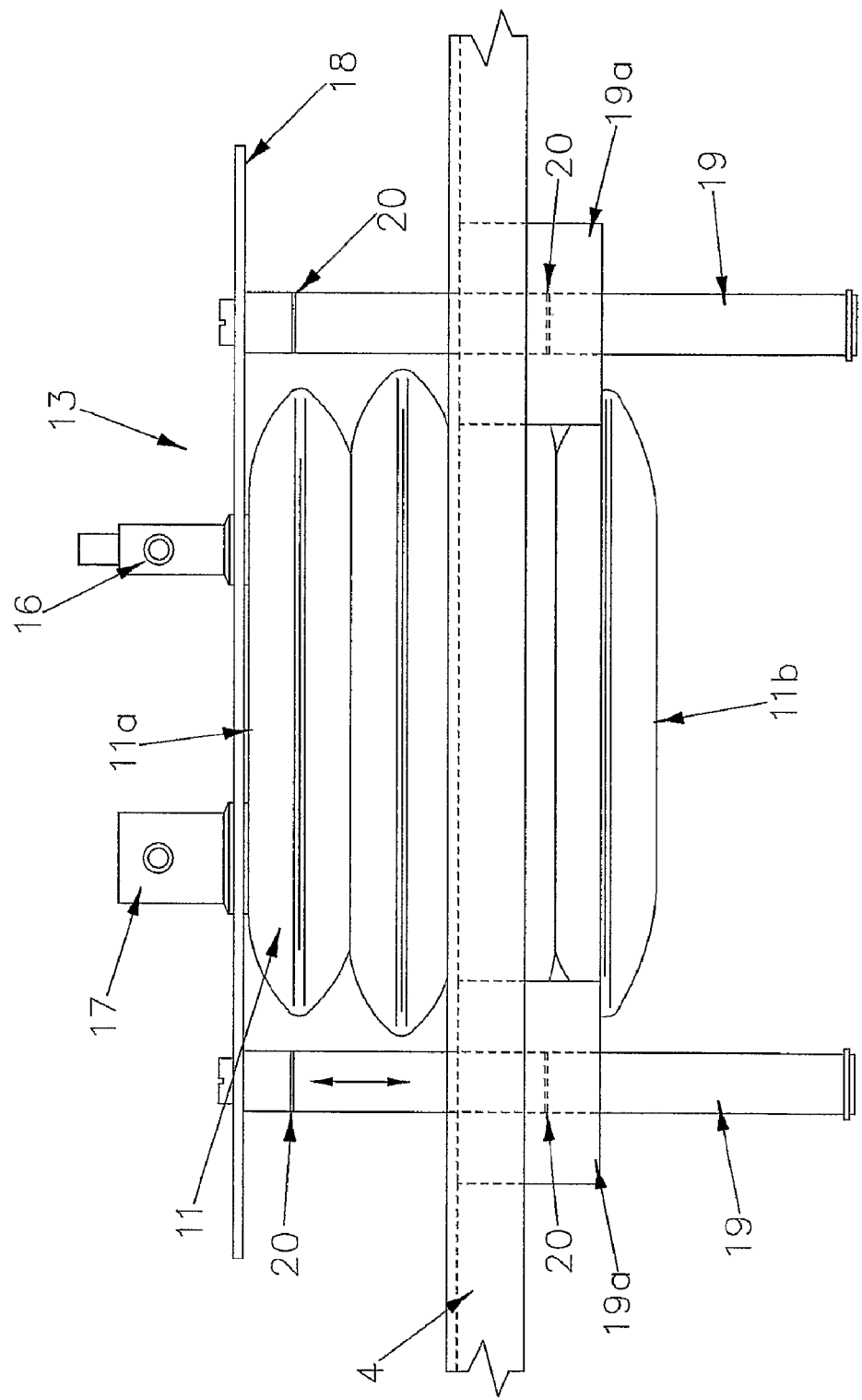

Referring in particular to FIGS. 1 and 3, one edge of the lid 13 is provided with an integrally formed extended portion 18 which lies flat on the upper surface of the top plate 4 when the bellows is in the collapsed position. The lid 13 is secured to the top plate 4 by means of a pair of spaced guide rods 19 which are mounted in blocks 19a on the underside of the top plate 4.

Each of the blocks 19a contains a ball and spring locking mechanism (not visible) which is arranged to bear against the side of the corresponding guide rod 19 and to lock against grooves 20 formed in the side of the rod. The lid 13 can be secured in this way in one of two positions:—with the lid 13 locked down to the top of the top plate 4, using the uppermost pair of grooves 20; with the lid 13 in the position depicted in FIG. 3, using the second pair of grooves 20.

In use, a face mask for administering CPAP is connected to the air outlet 17 by means of flexible tubing, and an air supply is connected to the air inlet 16, also by flexible tubing. Preferably, the flexible tubing connecting the air outlet 17 and the face mask is wide bore tubing, preferably 42 millimeter diameter. The tube may be formed with an inlet port for admitting medication into the airflow.

Either the mask or the mask tubing is provided with a negative pressure release valve, which opens as the pressure inside the mask/tube falls below ambient pressure. This ensures that the patient can breathe the surrounding air in the event of failure of the CPAP device, or loss of fresh gas flow.

Figure 4:
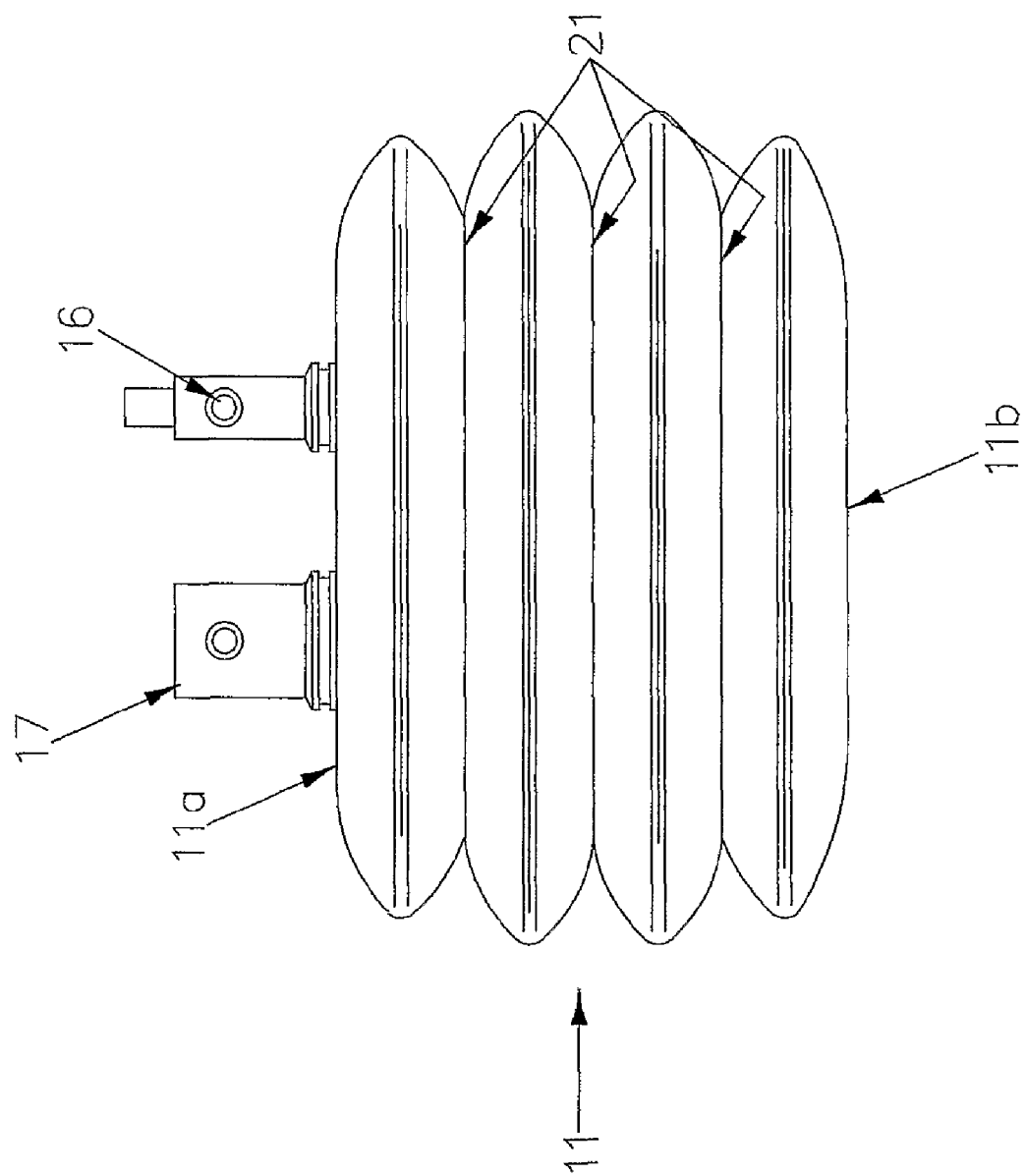

Referring in particular to FIGS. 3 and 4, the bellows 11 is a hollow container of flexible, airtight material. The bellows is oval in plan and from the side has a "Chinese lantern" shape, being formed with a series of equidistantly spaced constrictions 21, which help to retain the overall shape of the bellows when it is fully inflated. The top and bottom surfaces 11a, 11b respectively are substantially flat. Preferably, the bellows is made of an inexpensive plastics material which can be mass-produced with a high degree of accuracy, e.g. by a blow moulding process. For a majority of applications, the bellows is disposable. The material from which the bellows is made should be nonextensible and have no memory.

The inlet 16 and the outlet 17 preferably are moulded integrally with the bellows.

It is preferred that the shape and material of the bellows is such that the bellows are sufficiently flexible to be easily collapsed when removed from the device; this is desirable so that the bellows do not themselves cause any increase in the work of breathing of a patient. However, the upper and lower surfaces of the bellows must be of sufficient rigidity to support the inlet 16 and outlet 17, and to permit the uniform transmission of forces from the bellows support to the bellows. The bellows are preferably slightly convex in order to ensure an even distribution of the plastic during the blow-moulding process.

The connection between the lid 13 and the inlet 16 and outlet 17 supports the bellows from the top, and pressure is applied to the bellows from below by the lower support plate 10. This arrangement means that the device is minimally affected by gravity, so that the device can be operated in any of a wide range of different orientations, making it very suitable for emergency use.

The air contained in the bellows in use is compressed by the pressure applied to the lower surface of the bellows by the lower support plate 10, compressing the bellows 11 between the plate 10 and the lid 13. The lower support plate 10 is raised and lowered by a cable as described in detail below. The plate 10 is supported upon three pairs of hinges 24, only one of which is shown in FIG. 1, for clarity.

Figure 5:
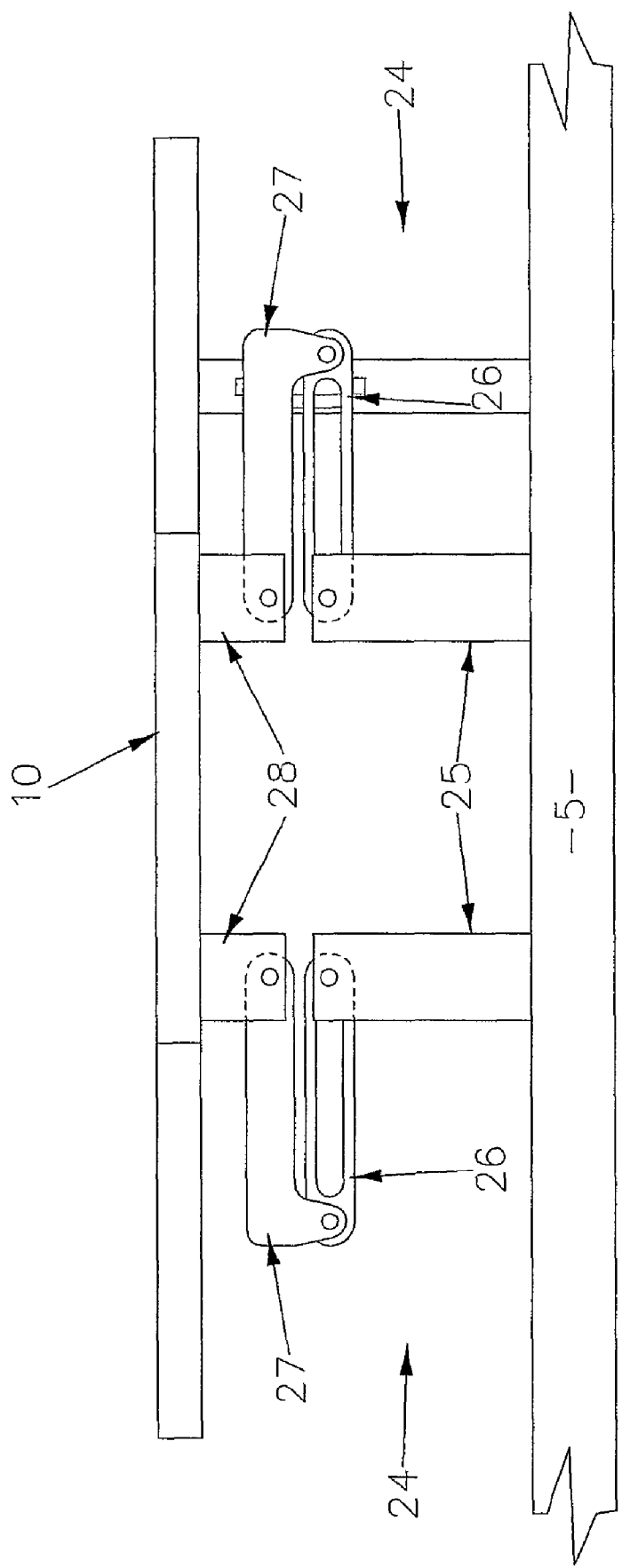

As shown on a larger scale in FIG. 5, each hinge 24 consists of a support block 25 which is secured to the upper surface of the baseplate 5 and extends at right angles to the plane of the baseplate 5. A first hinge arm 26 is pivoted at one end to the block 25 and at the other end to a second arm 27, the other end of which is pivoted to a block 28 which is rigidly secured to the underside of the plate 10. The pairs of hinges 24 are spaced around the periphery of the plate 10 so as to give a stable support to the plate as it is raised and lowered by the cable 23; the hinges 24 need not be equidistantly spaced.

The design and spacing of the hinges 24 is such that the plate 10 remains in a plane parallel to that of the top plate 4 at all times, thus ensuring that an even pressure is applied to the bellows 11 by the plate 10. However, this is not essential.

Figure 6:
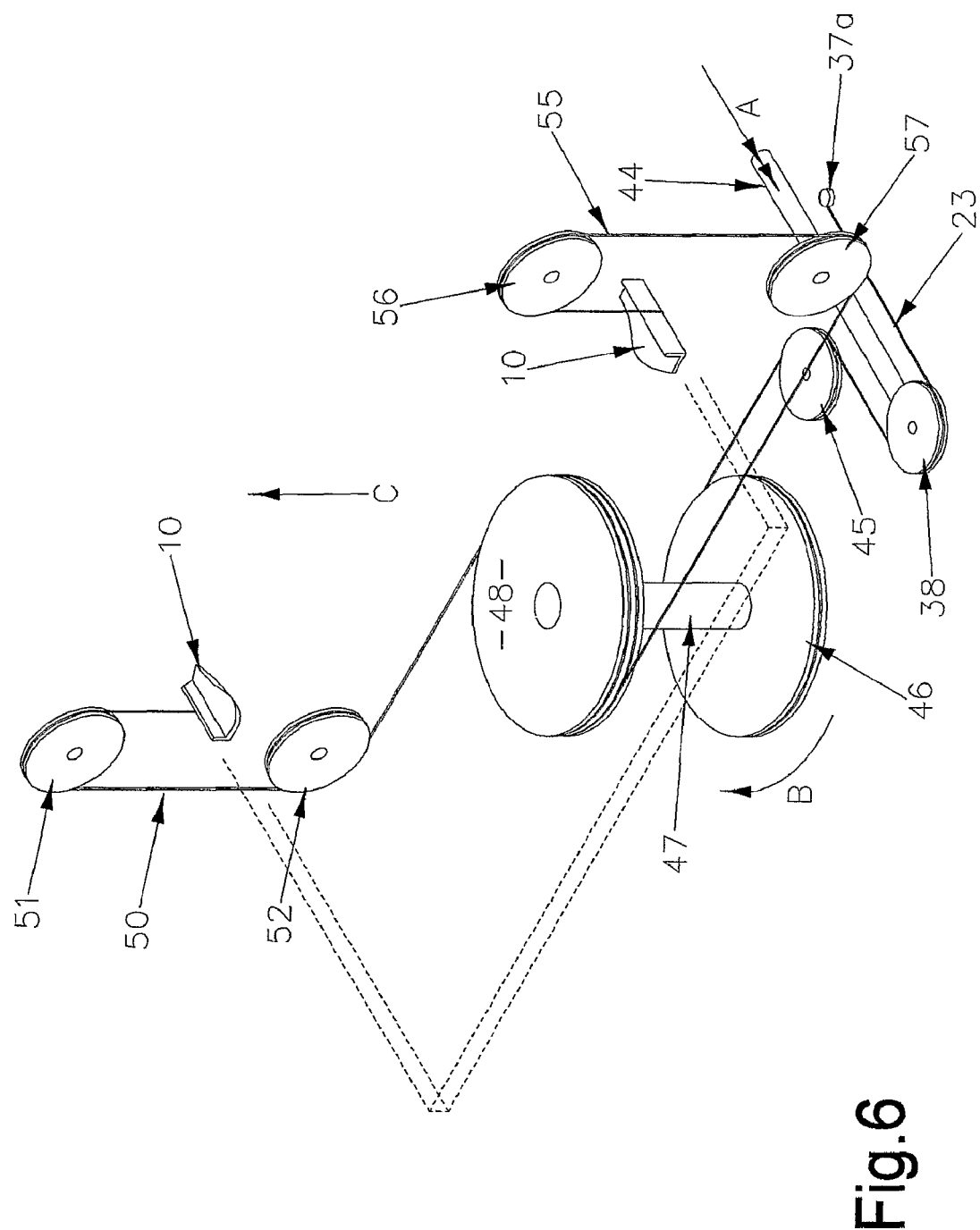

The system for moving the lower support plate 10 (and hence pressurising the bellows 11) is shown in detail in FIGS. 2 and 6. FIG. 2 shows the components of the pressurising system laid out in a single plane, for clarity and ease of description; most of these components are in fact secured to the upper surface of the baseplate 5, beneath the lower surface of the lower support plate 10, apart from the pressure gauges which are mounted on the upper surface of the top plate 4, for easy visibility.

Referring in particular to FIG. 2, the pressurising system consists of a high-pressure storage cylinder 30 which can be supplied with pressurised gas through an inlet 31, which is arranged to receive a commercially available pressurised gas capsule 32. The pressurised gas used may be any non-toxic gas e.g. helium, carbon dioxide. Alternatively, the housing may provide room for permanently fitting the capsule 32. The pressure of the gas in the high-pressure cylinder 32 is shown on the high-pressure gauge 33, which is mounted on the upper surface of the top plate 4.

The high-pressure cylinder 30 is connected to a pair of interconnected low pressure cylinders 34,35 via an adjustable regulator 36. The pressure in the low pressure cylinders 34,35 is shown by pressure gauge 33a, which also is mounted on the upper surface of the top plate 4. The low pressure cylinders 34 are connected to a pneumatic ram 37 which incorporates a rolling diaphragm attached to a piston, to minimise friction in the circuit, and thus minimise the imposed work of breathing by the patient in use.

One end of a first cable 23 is secured to the casing of the ram 37 at a securing point 37a and passes around a pulley 38 carried by the end of the ram. The cable 23 preferably is made of a low friction material.

The above described pneumatic circuit also incorporates safety valves 39,40 on the high-pressure and low pressure portions of the system respectively, and a pair of flow restrictors 41 between the high-pressure and low pressure portions of the system. To pass gas from the high-pressure cylinder 30 to the low pressure cylinders 34,35 a pressurising bleed valve 42 is activated manually. If it is necessary to lower the pressure in, or to depressurise, the low pressure part of the circuit, a blow down valve 43 is activated manually.

In use, a pressurised gas capsule 32 is used to pressurise the high-pressure cylinder 30 to a desired pressure, which is shown on the high-pressure gauge 33. Typically, the pressure is in the range 50-250 pounds per square inch. The regulator 36 is then adjusted manually as necessary to prevent over pressurising the low pressure cylinders 34,35, and then the bleed valve 42 is activated manually to pass gas from the high-pressure cylinder 30 to the low pressure cylinders 34,35, until these cylinders reach a desired pressure as indicated by low pressure gauge 33a. Typically, this pressure would be in the range 5-20 pounds per square inch. The pressure in the low pressure cylinders 34,35 automatically activates the pneumatic ram 37 to place a corresponding pressure on the bellows 11 via the cables and the plate 10.

The above described pressurising system could be varied in a number of ways; for example, a single low pressure cylinder could be used rather than a pair of low pressure cylinders. Further, the high-pressure cylinder 30 could be replaced by a commercially available pressurised gas capsule. Alternatively, the pressurised gas capsule 32 could be replaced by a connection for a small manually operated pump (such as a bicycle pump) which could be used to manually pressurise the high-pressure cylinder. This option obviously would be attractive if the device were to be used in remote locations where commercial gas capsules are not readily available.

If during use it is necessary to increase the pressure in the low pressure cylinders, the pressurising bleed valve 42 is operated until the required pressure is achieved. If it is necessary to decrease the pressure in the low pressure cylinders, then the blow down valve 43 is manually operated until the required pressure is achieved. The bleed valve 42 may be replaced with an adjustable regulator to allow the low-pressure cylinders to be maintained automatically at a predetermined pressure, from the high-pressure cylinder.

Referring to FIG. 6, the pneumatic ram 37 is not shown in full, but the securing point 37a of the first cable 23 and the ram arm 44 are shown. The first cable 23 passes around the pulley 38 on the outer end of the ram arm 44, around a pulley 45, and then around the lower pulley 46 of a cotton reel pulley 47. Two further cables are secured to the upper pulley 48 of the cotton reel pulley 47:—a second cable 50 is secured at one end to the lower surface of the lower support plate 10, is guided by pulleys 51 and 52, and then passes around one side of the pulley 48, to which the other end of the second cable 50 is secured. The third cable 55 is secured at one end to the lower surface of the lower support plate 10, at a position opposite to the securing point of the second cable 50, is guided by pulleys 56 and 57, and then passes around the opposite side of pulley 48 to cable 50, and is secured to that pulley. Since the cables 50,55 are secured to opposite sides of the pulley 48, rotation of the pulley 48 in either direction lengthens or shortens both cables 50,55, equally. Thus, movement of the ram arm 44 in the direction of Arrow A rotates the pulley 47 in the direction of Arrow B and shortens both cables 50 and 55, winding on to the pulley 48. Movement of the ram extension in the opposite direction lengthens both cables 50 and 55. When the cables 50,55 are shortened, they pull the support plate 10 upwards, in the direction of Arrow C, and thus increase pressure on the bellows 11. Lengthening the cables 50,55 lowers the support plate 10 and reduces the pressure on the bellows 11.

Figure 7:
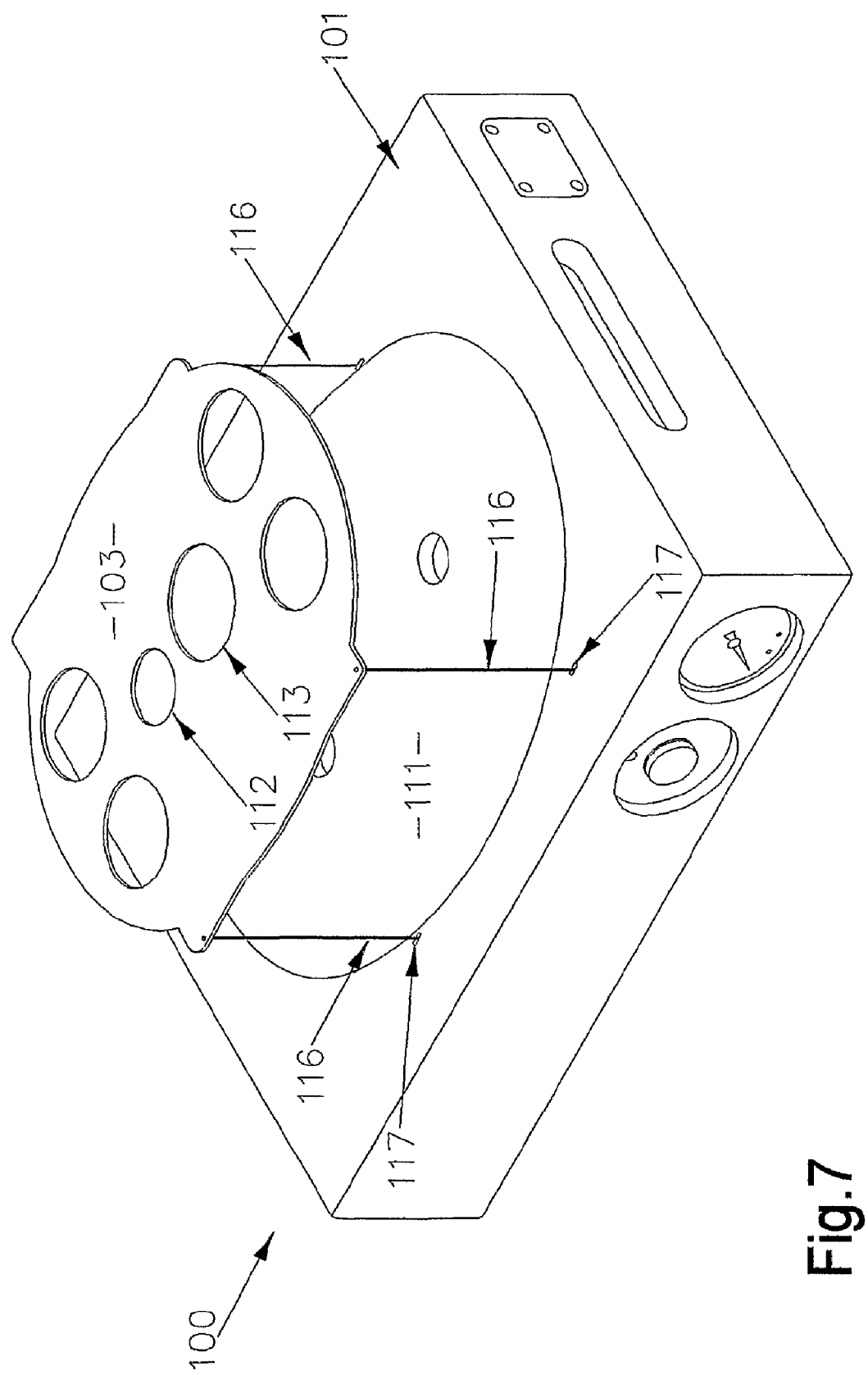
FIGS. 7-11 to a second embodiment.
Figure 8:
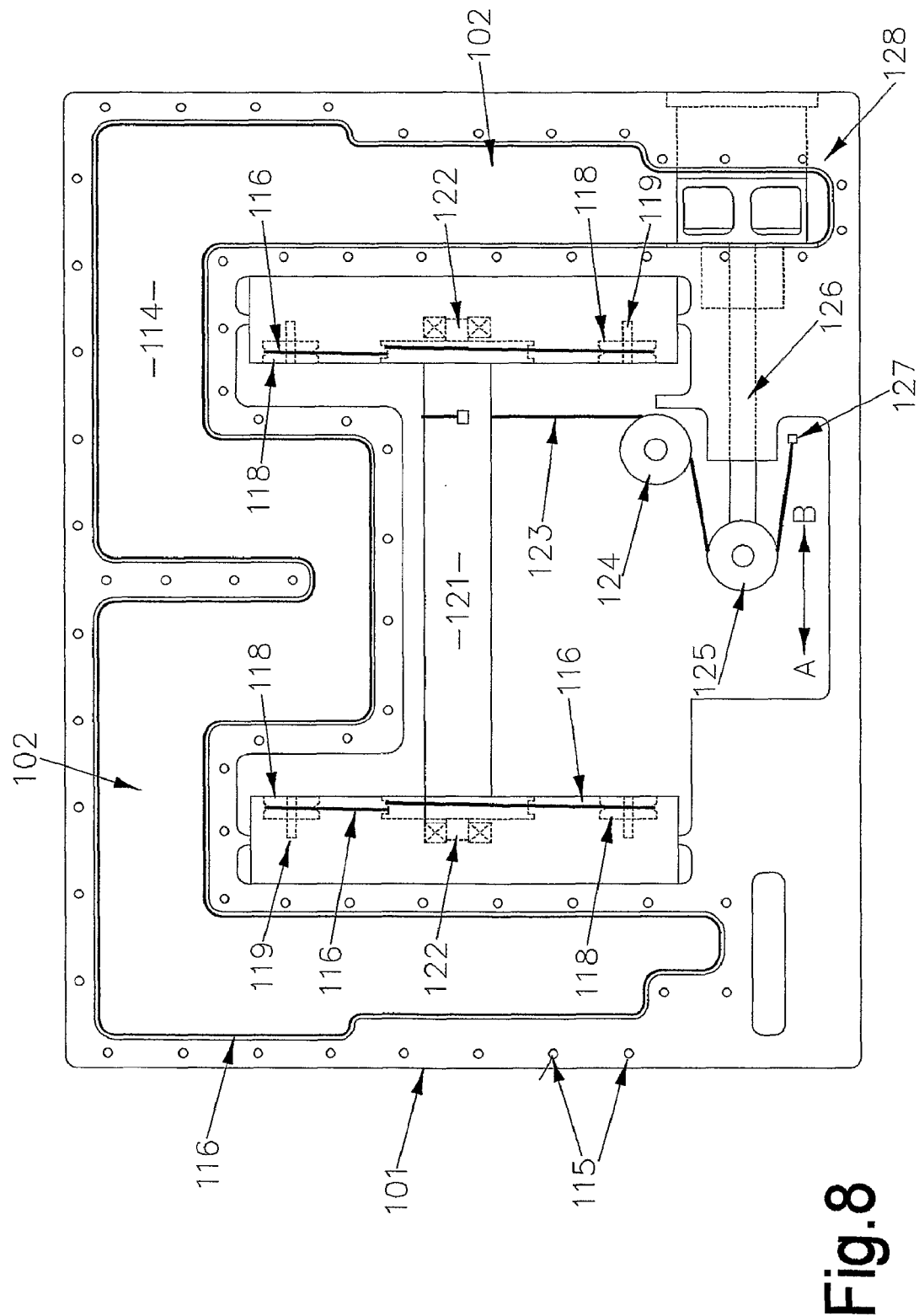
Figure 9:
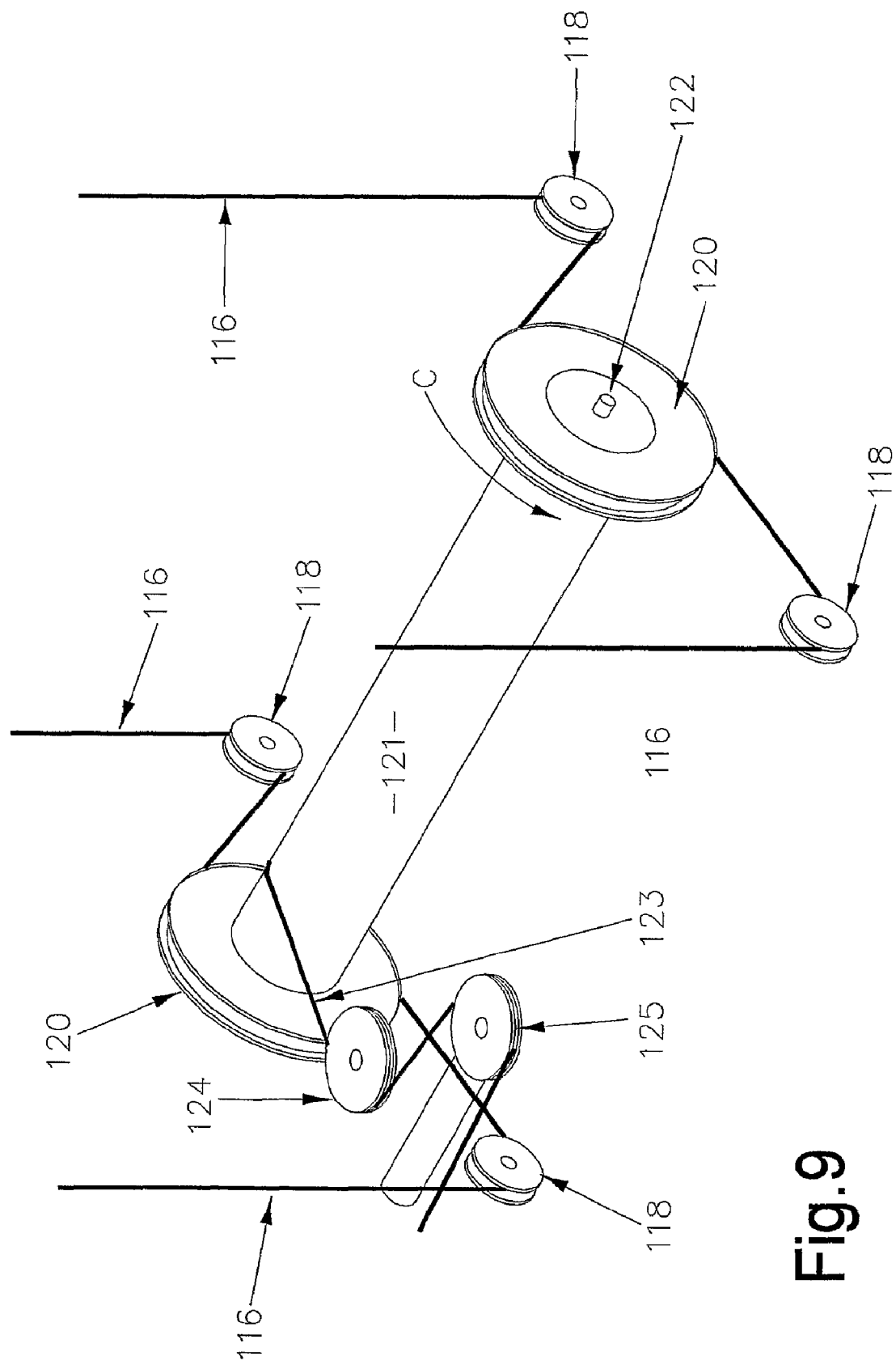
Figure 10:
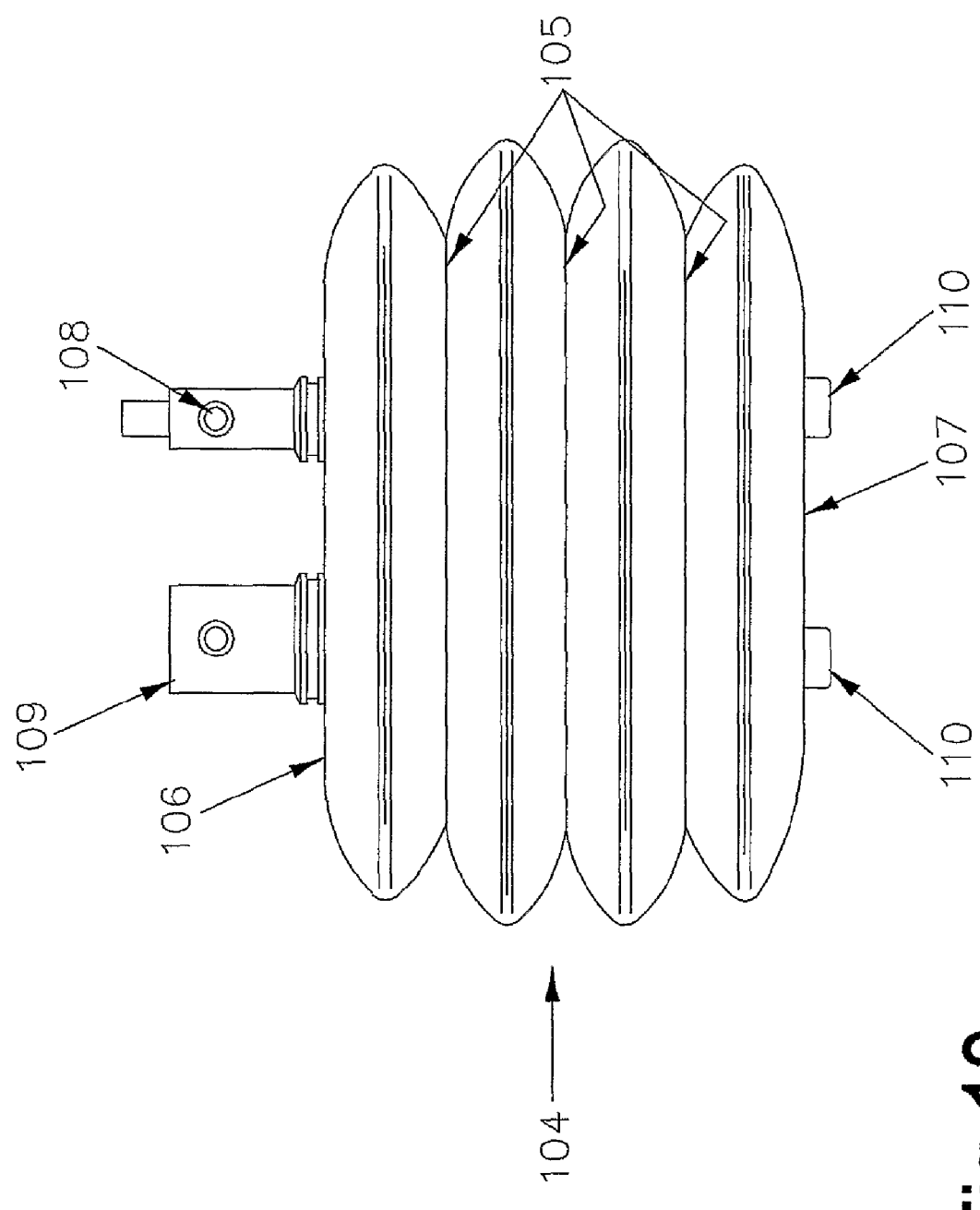

Referring to FIGS. 7-9, in a second embodiment of the invention, a CPAP device 100 includes a housing 101 which incorporates a pressurised gas reservoir 102 (FIG. 8), a pressure plate 103, and a breathable air reservoir 104.

The breathable air reservoir 104 is in the form of a bellows. The bellows 104 is a hollow container of flexible, airtight material which is inelastic and has no memory. For a majority of applications, the bellows is designed to be disposable and so preferably is made from an inexpensive plastic material which can be mass-produced with a high degree of accuracy e.g. by a blow moulding process.

The bellows 104 is oval in plan and from the side has a "Chinese lantern" shape, being formed with a series of equidistantly spaced constrictions 105 which operate to retain the overall shape of the bellows when it is fully inflated. The top and bottom surfaces 106/107 respectively are substantially flat except for an air inlet 108 and an air outlet 109 moulded integrally with the top surface 106, and two spaced locating lugs 110 moulded integrally with the bottom surface 107.

The shape and material of the bellows should be such that the bellows are sufficiently flexible to be easily collapsed when removed from the device; this is so that the bellows do not in themselves cause any increase in the work of breathing of a patient. However, the top surface of the bellows must have rigidity sufficient to support the air inlet and the air outlet, and to permit the uniform transmission of force from the pressure plate 103 to the bellows.

Figure 11:
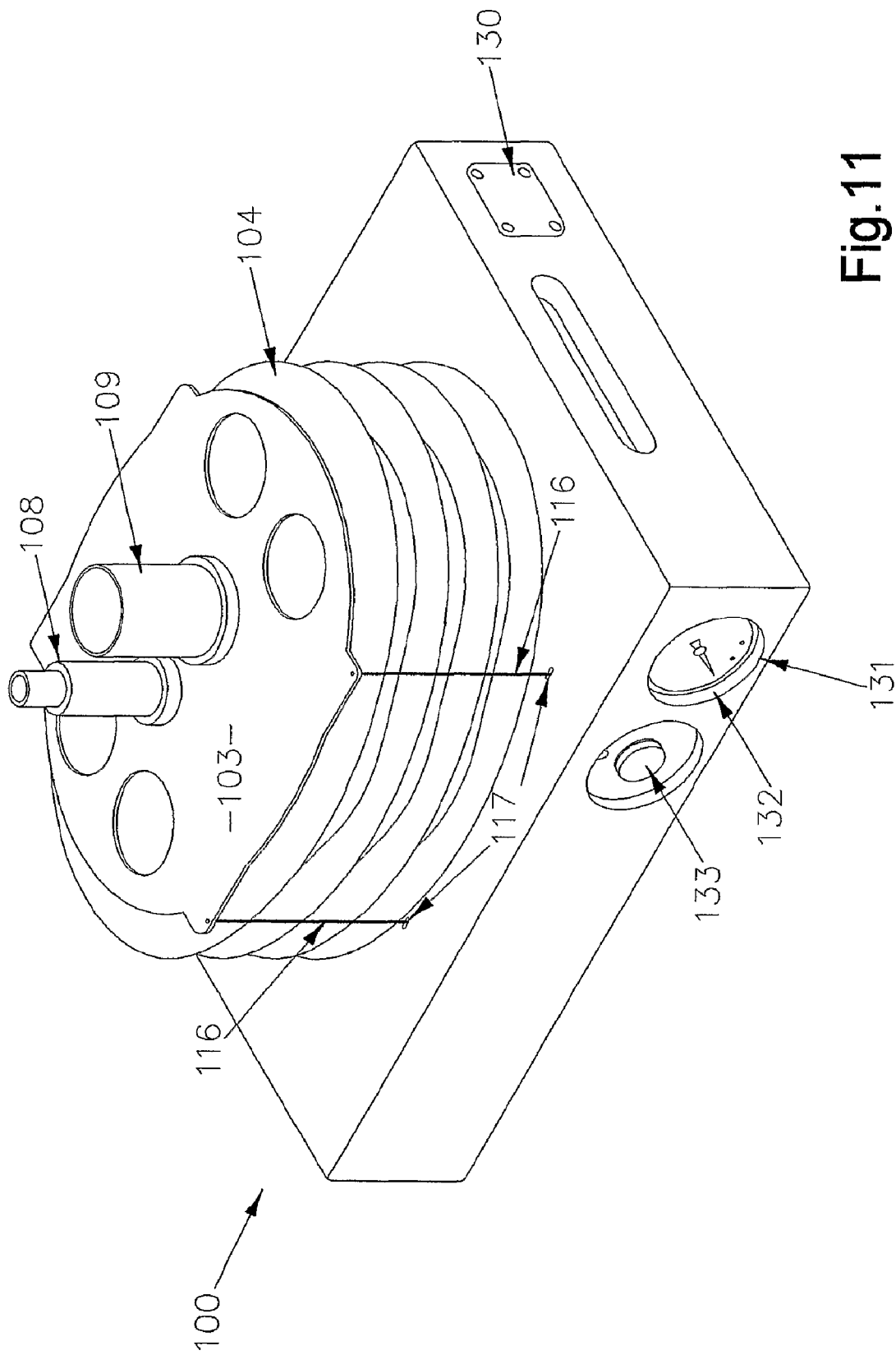

In use, the bellows 104 is located as shown in FIG. 11, with the bottom surface 107 of the bellows in contact with central area of the upper surface 111 of the housing 101, and the top surface 106 of the bellows in contact with the underside of the pressure plate 103, with the air inlet 108 and the air outlet 109 extending above the top surface of the pressure plate 103, through apertures 112 and 113 respectively.

Referring in particular to FIG. 8, the housing 101 is formed from a single block of material, a large part of which is hollowed out to form the pressurised gas reservoir 102. It is preferred that the pressurised gas reservoir is formed as a single large reservoir as shown, but it also would be feasible to form the pressurised gas reservoir as a series of smaller reservoirs interconnected by isolation valves. As shown, the pressurised gas reservoir is formed between the underside 114 of the upper surface 111 of the housing and a removable first cover (not shown) which is secured over the pressurised gas reservoir 102 by means of screws insert into a series of spaced apertures 115. The first cover when fully secured seals against a flexible O-ring seal 116 to give an airtight seal around the pressurised gas reservoir.

Another way of forming the pressurised gas reservoir is to insert a flexible airtight liner in the pressurised gas reservoir 102; this removes the requirement for the first cover to provide an airtight seal.

The remainder of the base of the housing 101 is covered by a second removable cover (not shown) which protects the pressure control equipment (described below) which is mounted in hollowed out portions of the housing 101.

As shown in FIGS. 9 and 11, pressure is applied to the pressure plate 103 by means of four cables 116 which are connected to the plate 103 at the corners of an imaginary rectangle. Each of the cables 116 is connected at one end to the pressure plate 103 and then passes through a slot 117 cut through the upper surface 111 of the housing 101, into the underside of the housing. If the CPAP device is to be used in out-of-hospital applications, the slots 117 are sealed by flexible gaskets. If necessary, each cable 116 may be protected by a sealed flexible plastics sleeve which allows free movement of the cable but protects it from dirt and contamination.

In the underside of the housing, each cable 116 passes around a small pulley 118 which is mounted for free rotation upon an axle 119 mounted in the housing (FIG. 8). The other end of each cable 116 is secured to one of two large pulleys 120 which are located one at each end of a shaft of 121. The large pulleys 120 are coaxial with the shaft 121 and the pulleys 120 and shaft 121 are mounted in the housing for free rotation about an axle 122. The shaft 121 is mounted centrally in the housing, midway between opposing pairs of pulleys 118, and the ends of the cables 116 coming from each pair of opposed pulleys 118 are secured on opposite sides of the pulleys 120 so that rotation of the pulley 120 in either direction tensions or slackens each of the associated cables 116 by an equal amount. Thus, rotation of the shaft 121 in either direction tensions or slackens all of the cables 116 by an equal amount and thus applies an even pressure to the pressure plate 103.

The shaft 121 is rotated by a control cable 123, one end of which is secured to the surface of the shaft. The control cable 123 then passes around a guide pulley 124, around a pulley 125 carried on the end of a piston 126, and the other end of the cable 123 is secured to an anchor 127 on the housing (FIG. 8 only). The piston 126 forms part of a pneumatic ram 128, which incorporates a rolling diaphragm (not visible) which is attached to the end of the piston 126 which lies within the pressurised gas reservoir 102. The piston 126 and the pulley 125 can move in the directions of arrows A and B in response to the pressure applied to the other end of the piston by the air in the pressurised gas reservoir.

The housing 101 is formed with a window (not shown) through the upper surface of the housing immediately above the pulley 125 on the end of the piston 126. The pulley 125 carries, or is marked with, an arrow and the underside of the window is marked with a gauge. As the piston 126 moves, the arrow moves relative to the gauge markings. The gauge markings are set to indicate the optimum working zone of the bellows, i.e. the zone in which the bellows are neither under- nor over-expanded:—if the position of the arrow relative to the gauge indicates that the bellows are over expanded, the pressure is reduced using a needle valve 133. If the position of the arrow relative to the gauge indicates that the bellows are under expanded, the pressure in the reservoir 102 is increased.

When the piston 126 and pulley 125 move in the direction of arrow A, the shaft 121 is rotated in the direction of arrow C by the control cable 123; the pulleys 120 rotate with the shaft 121, and apply a corresponding tension to each of the cables 116. This increases the pressure applied to the pressure plate 103, and hence the pressure applied to the bellows 104. When the piston 126 and pulley 125 move in the direction of Arrow B, the shaft 121 is rotated in the opposite direction and the pressure applied to the bellows 104 by the pressure plate 103 is reduced.

The pressurised gas reservoir 102 may be supplied with air or other gas (e.g. CO2, He) by any suitable means, e.g. a compressed air or compressed CO2 cartridge such as a commercially available pressurised gas capsule, or manual means such as a bicycle pump. Gas is supplied into the pressurised gas reservoir 102 through a valve (not visible) mounted behind removable plate 130 (FIG. 11). Alternatively, the interior of the housing may provide a permanent mounting for a pressurised gas cartridge. The pressure of the gas in the pressurised gas reservoir 102 is indicated by a gauge 131 of known type, which is mounted into an aperture 132 in the side wall of the housing. If necessary, excess pressure can be bled from the pressurised gas reservoir by means of the needle valve 133 mounted beside the gauge 131.

It should be noted that since the pressurised gas reservoir 102 has a very large capacity (typically about 100× the displacement volume of the pneumatic ram), the volume in the reservoir occupied by the end of the pneumatic ram 128 is negligible in comparison, so that movement of the piston of the pneumatic ram has no significant effect on the reservoir pressure.

In the embodiments, the bellows 11/104 may be used to humidify the airflow to the patient either by partially water-filling the bellows or by placing a water retaining device such as a wet sponge in the bellows. This would be externally or internally heated to provide up to 100% humidification at 37° C. Alternatively, a known humidifier (not shown) can be inserted in the air supply tubing between the air outlet and the face mask.

If required, the air supplied to the patient can be heated by an electrically heated hot plate beneath or within the bellows and/or by a heated wire along the air supply tubing.

In both of the above described embodiments, the bellows 11/104 can be varied in a number of ways:

1) The upper surface 11a/106 of the bellows may be made rigid or semi-rigid to form the "top plate" and the existing upper plates 13/103 respectively dispensed with. In the second embodiment, since the cables 116 are connected to the top plate 103, the stiffened upper surface of the bellows provides strong points to which the cables 116 could be secured.

Figure 12A:
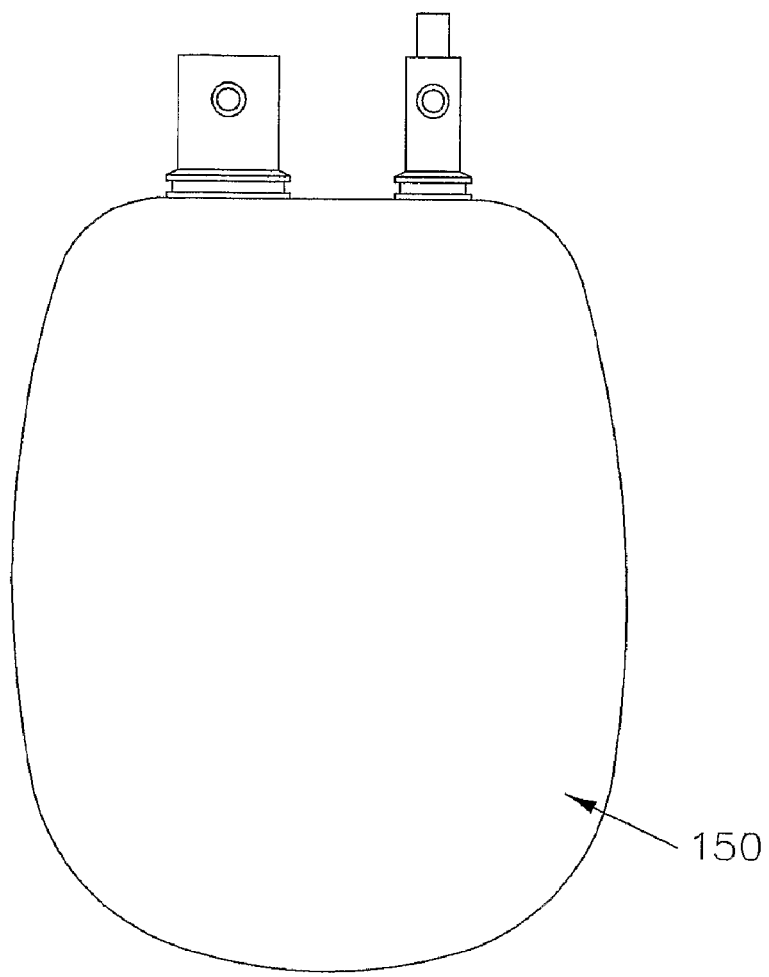
FIGS. 12a-c are side views of other forms of bellows.
Figure 12B:
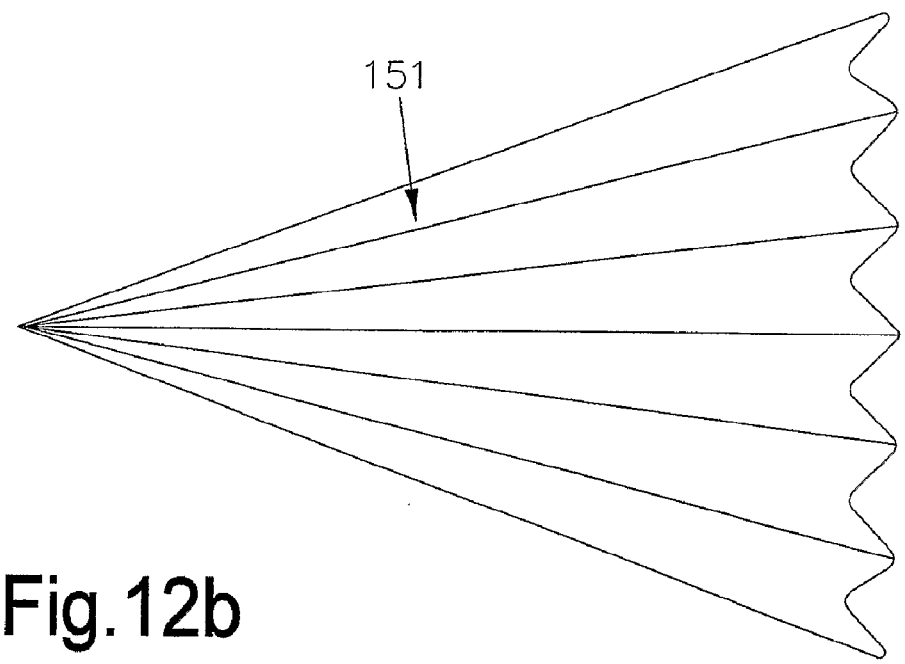

2. Because the pressurising system of the present invention is capable of pressurising the bellows to a substantially uniform pressure no matter what the shape or degree of inflation of the bellows, the bellows could be a simple airtight bag 150 (FIG. 12a) of any suitable flexible but inelastic material or could be shaped like a conventional fireside bellows 151 as shown in FIG. 12b.

Figure 12C:
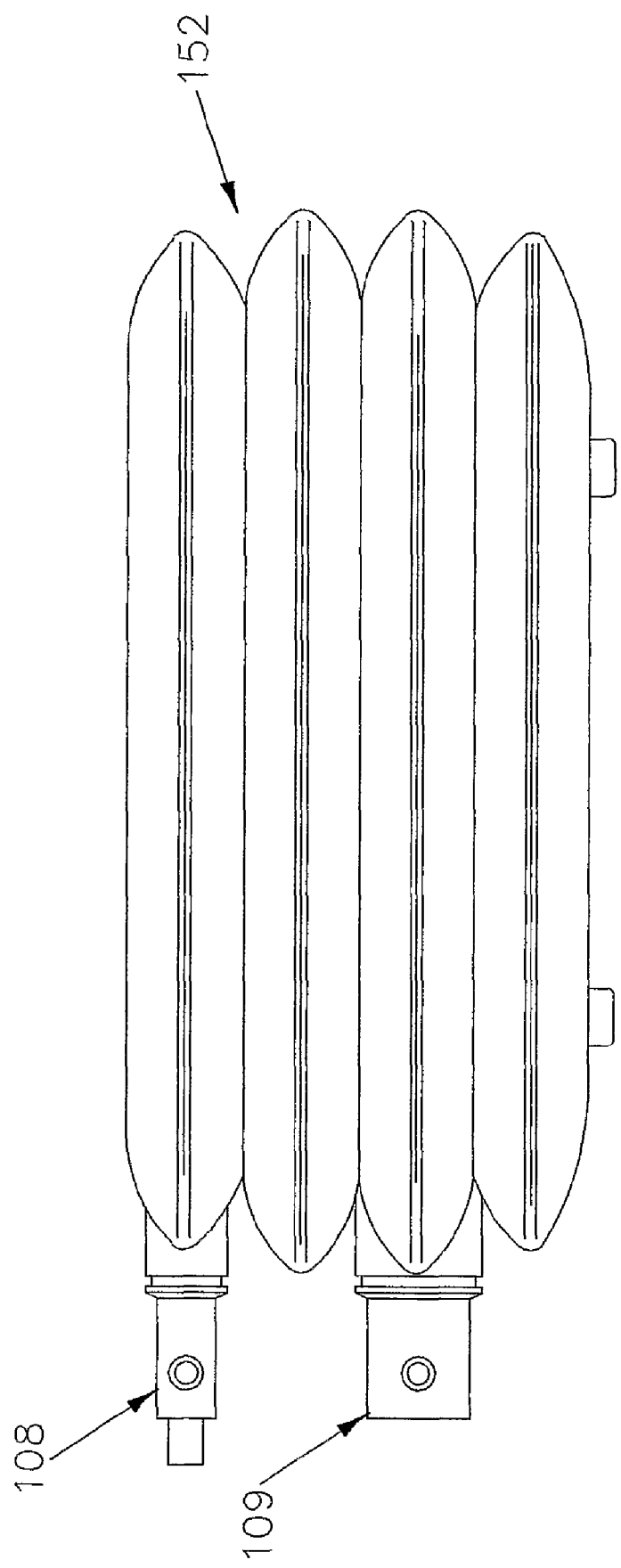

3. Alternatively the bellows 152 may have a generally flatter shape as shown in FIG. 12c, with the air inlet 108 and air outlet 109 coming out of the side of the bellows. This gives a CPAP device with a very low overall height.

4. The air inlet (16/108) to the bellows may be removed altogether, and the air supply connected to the tubing between the CPAP device and the patient delivery device (e.g. the mask), as described in NZ patent 511096/514278/515104.

Figure 13:
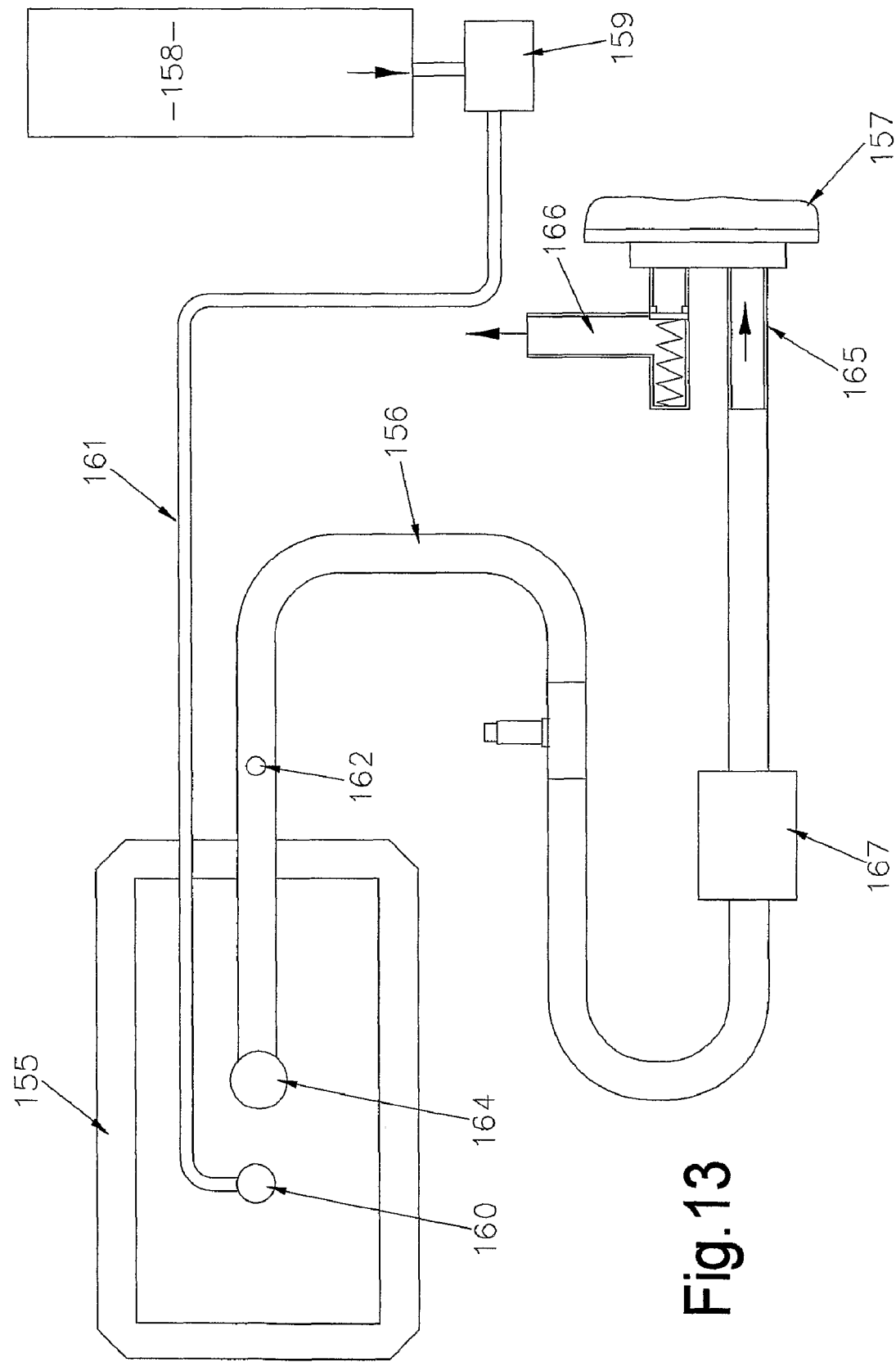
FIG. 13 is a diagrammatic plan view of a CPAP system incorporating the device of the present invention.

FIG. 13 shows, in diagrammatic plan view, a typical CPAP circuit:—a device 155 in accordance with either embodiment of the present invention is connected by a flexible air supply hose 156 to a patient delivery device in the form of a face mask 157, which may be of any suitable known type. Preferably, the flexible hose is wide bore tubing, e.g. about 42 millimeters diameter. Either the mask or the mask tubing is provided with a negative pressure release valve which opens if the pressure inside the mask/tube falls below ambient pressure. This ensures that the patient can breathe the surrounding air in the event of failure of the CPAP device or loss of fresh gas flow. A supply of oxygen (typically from a cylinder 158 at a pressure of 150 atmospheres regulated down to four atmospheres at the cylinder outlet) is connected to a Venturi 159 and then to the air inlet 160 into the breathable air reservoir (not shown) of the device 155, via an air inlet tube 161. The Venturi 159 entrains room air which mixes with the oxygen from the cylinder 158. The composition of the mixture may vary, (typical range 30%-100% oxygen) depending upon the patient's condition. The Venturi may be replaced by any of a range of air/oxygen blending devices. The air pressure in the breathable air reservoir is of course governed by the pressurising system, as described above. To avoid overpressure in the system and causing patient injury, a pressure release valve 162 is fitted to the air supply hose 156.

The mask 157 is fitted to the patient in known manner; once the mask is in place, the patient breathes normally. As the patient inhales, the oxygen/air mixture from the breathable air reservoir flows from the breathable air reservoir outlet 164 into the hose 156, through a humidifier 167, through the inlet 165 of the mask 157, and into the patient's lungs. The slight overpressure (i.e. pressure above atmospheric) in the breathable air reservoir makes it easier for the patient breathes and helps to expand the patient's lungs more fully. Further, the additional oxygen in the mix increases the proportion of oxygen available for uptake into the patient's bloodstream. However, because the breathable air reservoir is maintained at a substantially constant pressure, this minimises the pressure drop in the device when the patient inhales. As described above, the pressure in the pressurised gas reservoir translates to the pressure applied to the air in the breathable air reservoir. It follows that the pressure at which air can be supplied by the device to a patient can be varied by varying the pressure of the air in the pressurised gas reservoir to suit the requirements of each patient.

When the patient exhales, the exhaled air is expelled through the exhaust valve 166 of the mask; the exhaust valve may be of any suitable known type. The slight overpressure in the hose 156 and the breathable air reservoir prevents the exhaled gases from passing back into the hose 156.

In practice, the doctor supervising a patient would decide what level of CPAP was needed, and select a mask exhaust valve for that level of air pressure. The pressure in the breathable air reservoir of the CPAP device would then be adjusted to give the required pressure, by adjusting the pressure in the pressurised gas reservoir.

The above described arrangement may be varied by bringing the oxygen enriched air from the tube 161 directly into the outlet tube 156, and omitting the inlet 160.

Normally, the mask, hose and bellows all would be single-use only and would be removed for disposal after each use. Once the hose and bellows have been removed, the first embodiment may be secured for transport by locking the lid 13 down to the top of the top plate 4; the second embodiment may be secured for transport by securing the pressure plate 103 against the upper surface 111 of the housing.

Figure 14:
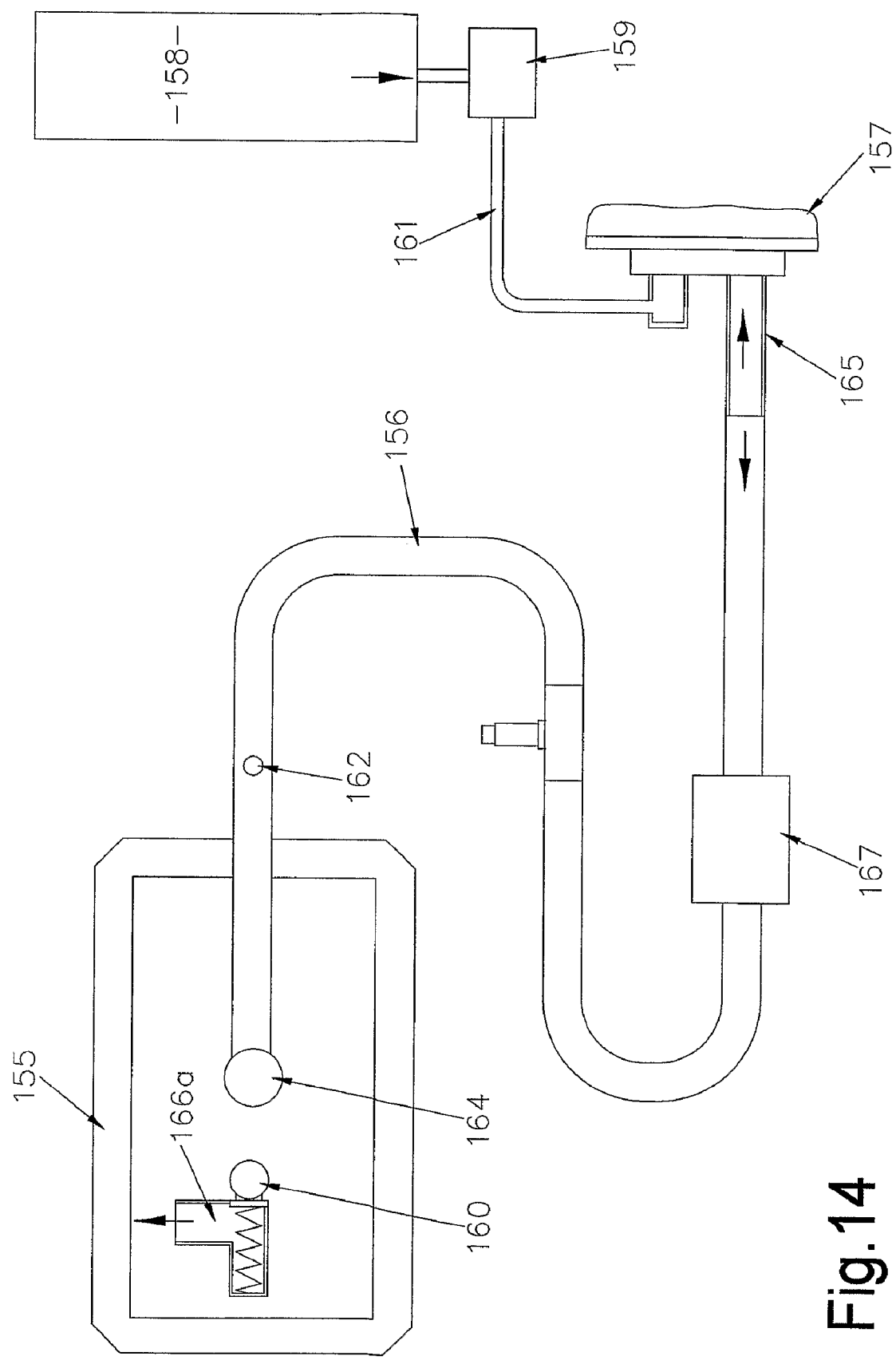
FIG. 14 is a diagrammatic plan view of a ventilator system incorporating the device of the present invention.

A further adaptation is required if the device is to be used as a ventilator; this variant is shown in FIG. 14. In this case, the oxygen or oxygen enriched air supplied through the hose 161 enters the system at or near the mask 157 and the exhaust valve 166 is removed from the mask.

An exhaust valve 166a is fitted to the breathable air reservoir. The valve 166a is a known type capable of being switched between two different levels of pressure, and is set to automatically switch between the two available levels. This gives the equivalent to a Mapleson D circuit:—a patient unable to breathe on their own is supplied with oxygen enriched air through the hoses 161 and 165; overflow from the hose 161, plus backflow from the mask 157 fills the breathable air reservoir through the hose 165 and the outlet 164.

The switching of the valve 166a between two different pressure levels actively assists in removing carbon dioxide from the patient's lungs.

For normal conditions of usage, the device of the present invention is pre-calibrated for use in a temperature range 5° C.-30° C. Gas pressure is dependent upon temperature, but for this small temperature range, the pressure variations caused by temperature fluctuations are so small as to be safe to ignore for practical purposes. However, if the device of the present invention is to be used at substantially higher or substantially lower temperatures, then it must be recalibrated to allow for the effect of the air temperature on the gas pressure.

The invention claimed is:

1. A continuous positive airway pressure device which includes:
    an inflatable breathable air reservoir provided with an air inlet/outlet;
    a pressurised gas reservoir arranged to apply a predetermined substantially constant pressure on the breathable air reservoir, irrespective of the degree of inflation of the breathable air reservoir;
wherein the pressurised gas reservoir in use only pressurises the breathable air reservoir and does not supply gas to the breathable air reservoir.

2. The device as claimed in claim 1 wherein the pressurised gas reservoir applies said predetermined pressure on the breathable air reservoir by means of:
    a pneumatic ram which is operable by the pressurised gas reservoir; and
    load transmitting means connected to the pneumatic ram.

3. The device as claimed in claim 2 wherein the pneumatic ram incorporates a rolling diaphragm.

4. The device as claimed in claim 2 wherein said load transmitting means includes a movable plate which is arranged to apply pressure on the breathable air reservoir.

5. The device as claimed in claim 2 or claim 4 wherein said load transmitting means includes cables and pulleys.

6. The device as claimed in claim 4 wherein said load transmitting means further includes cables and pulleys, one or more cables being connected between the movable plate and the pneumatic ram such that reciprocation of the pneumatic ram causes a corresponding movement of the plate.

7. The device as claimed in claim 6 wherein the movable plate contacts the upper surface of the breathable air reservoir.

8. The device as claimed in claim 6 wherein the movable plate contacts the lower surface of the breathable air reservoir.

9. The device as claimed in claim 8 wherein the movable plate is supported upon spaced hinges.

10. The device as claimed in claim 4 wherein the movable plate is selected from the group consisting of: a rigid solid plate, a flexible solid plate, a rigid mesh plate and a flexible mesh plate.

11. The device as claimed in claim 1 wherein the pressurised gas reservoir includes at least one low pressure reservoir.

12. The device as claimed in claim 11 wherein the pressurised gas reservoir further includes a high-pressure reservoir which is connectable to said at least one low pressure reservoir.

13. The device as claimed in claim 12 wherein said high-pressure reservoir comprises a pressurised gas capsule.

14. The device as claimed in claim 12 wherein the pressurised gas reservoir further includes a pressurised gas capsule which is connectable to said high-pressure reservoir.

15. The device as claimed in claim 12 wherein the pressurised gas reservoir provides a connection for a manual pump.

16. The device as claimed in claim 1 wherein the pressurised gas reservoir is provided with a pressure gauge.

17. The device as claimed in claim 12 wherein each of the high-pressure reservoir and at least one of the low pressure reservoirs are provided with separate pressure gauges.

18. The device as claimed in claim 1 wherein the pressurised gas reservoir is formed within a protective housing which also supports the breathable air reservoir.

19. The device as claimed in claim 1 wherein the air inlet and the air outlet are combined.

20. The device as claimed in claim 1 wherein the air inlet and the air outlet are separate.

21. The device as claimed in claim 1 wherein the breathable air reservoir is made of a flexible but inelastic material.

22. The device as claimed in claim 1 wherein the breathable air reservoir is selected from the group consisting of: a bellows having equidistantly spaced constrictions and a flat top and base, a bag, and a fireside bellows shape.

23. The device as claimed in claim 22 wherein the upper surface of the breathable air reservoir is rigid or semi rigid.

24. The device as claimed in claim 1 wherein the breathable air reservoir is adapted to contain water for humidifying the breathable air flow from the reservoir.

25. The combination of a device as claimed in claim 1 and a hose connected at one end to the air inlet/outlet of the breathable air reservoir and at the other end to a mask.

26. The combination as claimed in claim 25 wherein the hose is a wide bore hose, having an internal diameter in the range 30-55 millimeters.

27. The combination as claimed in claim 25 further including an exhaust valve fitted to the mask.

28. The combination as claimed in claim 25 further including a two level exhaust valve fitted to the air inlet of the breathable air reservoir.

* * * * *